(12) United States Patent
Boskamp (10) Patent No.: US 11,062,891 B2
(45) Date of Patent: Jul. 13, 2021

(54) EVALUATION OF COMPLEX MASS SPECTROMETRY DATA FROM BIOLOGICAL SAMPLES

(71) Applicant: Bruker Daltonik GmbH, Bremen (DE)

(72) Inventor: Tobias Boskamp, Worpswede (DE)

(*) Notice: Subject to any disclaimer, the term of this patent is extended or adjusted under 35 U.S.C. 154(b) by 0 days.

(21) Appl. No.: 16/826,966

(22) Filed: Mar. 23, 2020

(65) Prior Publication Data

US 2020/0328069 A1 Oct. 15, 2020

(30) Foreign Application Priority Data

Apr. 12, 2019 (DE) .......................... 102019109771-1

(51) Int. Cl.
| | | |
|---|---|---|
| *H01J 49/00* | (2006.01) | |
| *G16B 40/10* | (2019.01) | |

(Continued)

(52) U.S. Cl.
CPC ........ *H01J 49/0036* (2013.01); *G01N 24/087* (2013.01); *G01N 29/46* (2013.01); *G01N 33/4833* (2013.01); *G01N 33/5008* (2013.01); *G01N 33/53* (2013.01); *G01N 33/6848* (2013.01); *G16B 40/10* (2019.02); *H01J 49/0004* (2013.01); *H01J 49/0009* (2013.01); *G01N 2223/423* (2013.01); *G01N 2496/25* (2013.01)

(58) Field of Classification Search
CPC ............. H01J 49/0036; H01J 49/0004; H01J 49/0009; H01J 49/40; G16B 40/10; G01N 33/6848; G01N 33/6851; G01N 33/4833; G01N 33/5008; G01N 33/53; G01N 27/64; G01N 24/087; G01N 29/46; G01N 2496/25; G01N 2223/423
USPC ......................................................... 250/282
See application file for complete search history.

(56) References Cited

U.S. PATENT DOCUMENTS

| | | |
|---|---|---|
| 3,069,654 A | 12/1962 | Hough |
| 2005/0042771 A1* | 2/2005 | Koster ................. C07D 519/00 436/518 |

(Continued)

FOREIGN PATENT DOCUMENTS

DE 102016012302 A1 4/2018

OTHER PUBLICATIONS

Wolski et al., "Calibration of mass spectrometric peptide mass fingerprint data without specific external or internal calibrants." BMC Bioinformatics 6:203, 2005.

(Continued)

*Primary Examiner* — Kiet T Nguyen
(74) *Attorney, Agent, or Firm* — Benoit & Côté Inc.

(57) ABSTRACT

The disclosure relates to a method which is suitable for the quality control and signal correction of mass spectrometry data of biological tissue samples and is based on the analysis of the chemical background signal observed in a spectrum. It exploits the fact that the chemical background signal contains components from a plurality of polymer molecules, whose chemical structure has strong regularities. These regularities mean that the observed masses are subject to certain statistical distributions, which are each characteristic of the class of molecule. By analyzing these statistical properties, it is possible to detect and correct any mass shifts which may be present.

20 Claims, 8 Drawing Sheets

(51) Int. Cl.
  *G01N 33/68* (2006.01)
  *G01N 24/08* (2006.01)
  *G01N 33/483* (2006.01)
  *G01N 33/50* (2006.01)
  *G01N 33/53* (2006.01)
  *G01N 29/46* (2006.01)

(56) References Cited

U.S. PATENT DOCUMENTS

| | | |
|---|---|---|
| 2007/0038387 A1 | 2/2007 | Chen et al. |
| 2012/0232805 A1 | 9/2012 | Sadygov |
| 2017/0221687 A1 | 8/2017 | Stauber et al. |
| 2018/0019110 A1 | 1/2018 | Kubo |
| 2019/0257839 A1 | 8/2019 | Boskamp |

OTHER PUBLICATIONS

Senko et al. "Determination of monoisotopic masses and ion populations for large biomolecules from resolved isotopic distributions." Journal of the American Society for Mass Spectrometry 6(4), 1995, pp. 229-233.

Mitra, Indranil et al., Anal. Chem., Mar. 20, 2012, 20; 84 (6) 3026-3032.

Drake, R. R. et al., "MALDI Mass Spectrometry Imaging of N-Linked Glycans in Cancer Tissues." Advances in Cancer Research 134, 2017, pp. 85-116.

Wolski, W. E., et al., "Analytical model of peptide mass cluster centres with applications." Proteome Sci 4: 18, 2006.

Hoshida et.al., "Integrative Transcriptome Analysis Reveals Common Molecular Subclasses of Human Hepatocellular Carcinoma", Cancer Res. Sep. 15, 2009, 69(18), pp. 7385-7392.

Bowers et.al., "A MALDI Imaging Mass Spectrometry Workflow for Spatial Profiling Analysis of N-linked Glycan Expression in Tissues", Anal. Chem., Oct. 15, 2013, 85(20), pp. 9799-9806.

\* cited by examiner

EVALUATION OF COMPLEX MASS SPECTROMETRY DATA FROM BIOLOGICAL SAMPLES

BACKGROUND OF THE INVENTION

Field of the Invention

The invention relates to a method which is suitable for the quality control and signal correction of mass spectrometry data from biological tissue samples and is based on the analysis of the chemical background signal observed in a spectrum.

Description of the Related Art

The prior art is explained below with reference to a special aspect. This shall not be understood as a limitation, however. Useful further developments and modifications of what is known from the prior art can also be used above and beyond the comparatively narrow scope of this introduction, and will easily be evident to the expert skilled in the art in this field after reading the following disclosure.

During the acquisition of MALDI-TOF mass spectrometry data from biological tissue sections (matrix-assisted laser desorption/ionization Time-of-flight=MALDI-TOF), a large amount of information on the molecular structure of the tissue samples is obtained. At the same time, a number of potential interferences affect the measurement, which can lead to distortions and errors in the information gained.

A frequently occurring distortion of the data measured consists in a systematic error in the masses measured. In many cases, conventional methods to correct such mass distortions are either too imprecise or too time-consuming, or require operator intervention and cannot therefore be automated.

The mass of a molecule is given in daltons (Da) as a multiple of the atomic mass unit (1 Da=1 amu, atomic mass unit). The relative measurement error for MALDI-TOF measurements is typically in the order of 50-100 ppm (ppm=parts per million). In the mass range up to 3,000 daltons which is relevant for many tasks, the error is therefore frequently below 0.5 daltons, but it can also exceed this limit in individual cases.

The distortion of the mass axis resulting from the measurement errors is usually compensated by a calibration, which involves placing a calibration solution next to or on the tissue sample. After the measurement, the spectra measured are compared with the expected masses of the known constituents of the solution, and a calibration curve is determined from this (see Christian, N. P., R. J. Arnold and J. P. Reilly (2000): "Improved calibration of time-of-flight mass spectra by simplex optimization of electrostatic ion calculations." Anal. Chem. 72(14): 3327-3337).

For practical reasons, a calibration solution can only contain a small number of known substances. This limits the number of interpolation points from which the calibration curve is determined, and thus the accuracy of the calibration. This form of calibration, moreover, requires manual user interaction and incorrect assignments are possible.

In contrast, methods of statistical peptide calibration are fully automatic and do not require a calibration solution (see Wool, A and Z. Smilansky (2002): "Precalibration of matrix-assisted laser desorption/ionization-time of flight spectra for peptide mass fingerprinting." Proteomics 2(10): 1365-1373; and Wolski, W. E., M. Lalowski, P. and K. Jungblut and K. Reinert (2005): "Calibration of mass spectrometric peptide mass fingerprint data without specific external or internal calibrants." BMC Bioinformatics 6: 203). With these methods, the correction is performed by comparing the masses measured in the tissue with a theoretical peptide mass model and a peptide database. This approach can therefore only be applied to peptides and requires prior "peak picking", i.e. identification of relevant mass signals in a spectrum which stand out from the electronic noise. These methods can also lead to erroneous results due to an incorrect assignment between mass signal and peptide database.

In a related method of mass shift normalization of peptide spectra developed by the inventor (see WO 2018/072862 A1; PCT/EP2017/001131), ensembles of spectra are considered and each modified so as to minimize the relative mass shifts between the spectra. This is achieved by evaluating and comparing statistical characteristics of the background signals with each other, from which correction transforms for each individual spectrum are then derived. This fully automatic method can be implemented efficiently and does not require peak picking, but is only suitable for peptide data.

In MALDI-TOF mass spectrometry, a biological tissue sample is coated with matrix solution, after suitable sample preparation, and then bombarded with a laser in a vacuum (see Caprioli, R. M., T. B. Farmer and J. Gile (1997): "Molecular imaging of biological samples: localization of peptides and proteins using MALDI-TOF MS." Anal. Chem. 69(23): 4751-4760). Molecules are thereby extracted from the tissue and ionized, typically with a single positive charge. The ions are subsequently accelerated in an electric field and registered by a detector. The m/z value, i.e. the mass-to-charge ratio of the molecule, can be determined from the time-of-flight. The mass spectrum measured represents the relative number of registered ions (spectral intensity) as a function of their m/z values. Assuming a single positive ionization, the m/z-value is identical with the mass of the ionized molecule. Accordingly, the term mass is often used in the further description below for reasons of simplicity, even though it is actually the mass-to-charge ratio m/z which is meant.

The molecules observed can belong to different classes of molecules. Depending on the application, metabolites, lipids, peptides, proteins and carbohydrates (glycans) in particular are investigated (see Spengler, B. (2015): "Mass spectrometry imaging of biomolecular information." Anal. Chem. 87(1): 64-82), frequently from a two-dimensional tissue section in an imaging method (MSI=mass spectrometry imaging). The preparation method and measurement parameters used in each case have a big impact on which classes of molecules are ionized in which mass ranges and appear in the spectra measured.

The mass m of a molecule in daltons corresponds approximately to the total number of protons and neutrons of which the atoms of the molecule are composed. The difference between this integer nominal mass $m_N$ and the actual exact mass m is called the mass defect. The mass defect of a molecule is the sum of the mass defects of the individual atoms, which in turn are different for each chemical element or isotope.

The mass defect of the lighter elements up to nitrogen is positive, and identical to zero at carbon because of the definition of the atomic mass unit. It is negative for oxygen and all heavier elements. In biochemistry, the total mass defect of most organic compounds is positive.

Figure 1:
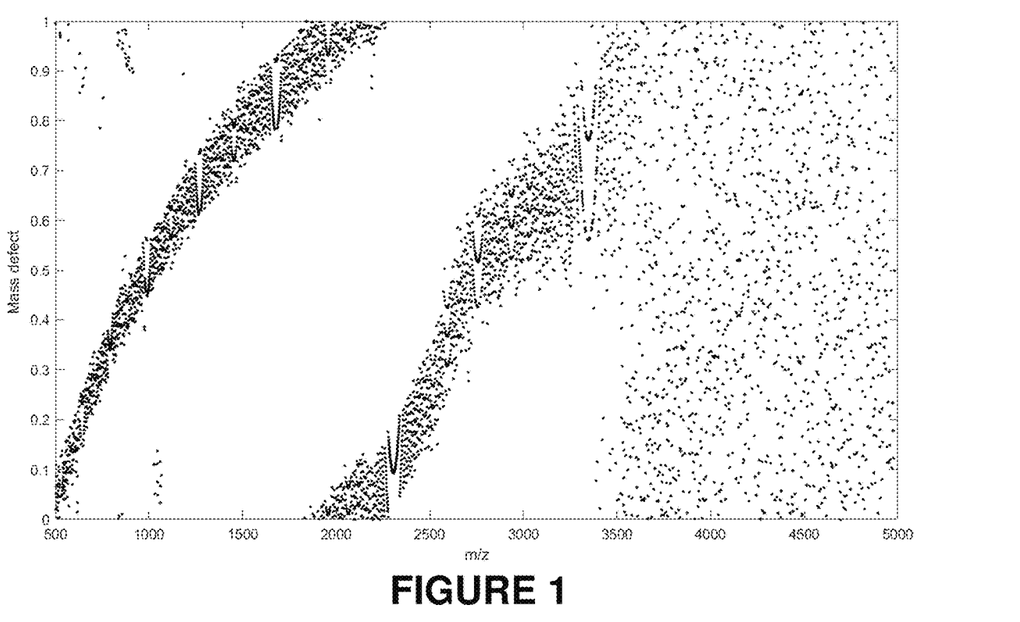
FIG. 1 shows a conventional mass defect diagram of an average spectrum with a recognizable peptide band (Prior Art).

To visualize the mass defects observed in a spectrum, the m/z values of the mass signals found in a spectrum are plotted in a diagram, whose horizontal axis corresponds to the mass m (or the m/z value), while their decimal places $\varphi(m)=m-\text{floor}(m)$ are plotted on the vertical axis (see FIG. 1). It should be noted that the mass defect of larger molecules can have values which are greater than one dalton and therefore the non-integer portion of a mass does not have to agree with its mass defect.

So-called Kendrick diagrams (see Kendrick, E. (1963): "A Mass Scale Based on CH2=14.0000 for High Resolution Mass Spectrometry of Organic Compounds." Anal. Chem. 35(13): 2146-2154) are a variant of this representation, where a scaling factor A is selected such that it corresponds to the ratio of exact mass and nominal mass of a specific group of atoms. This is typically a group of atoms which occurs as a repeat unit in a class of polymers under consideration. The quantity $$\Delta_\lambda(m) = \varphi\left(\frac{m}{\lambda} + \frac{1}{2}\right) - \frac{1}{2}$$

is plotted on the vertical axis in the Kendrick diagram, and is termed a Kendrick shift below. Since $\Delta_\lambda(m)=\Delta_\lambda(m+\lambda n)$, this means that for integer n, $\Delta_\lambda$ assumes identical values for molecules which differ only by one or more repeats of the group of atoms considered. The Kendrick shift is therefore a measure of how much the mass of a molecule differs from the masses of a specific polymer family. It can have values in the range $[-\frac{1}{2} \ldots +\frac{1}{2}]$, where the two ends of this range must be considered to be identified with each other. The Kendrick shift scale thus corresponds topologically to a circle.

Peptides (and their larger equivalents: proteins) are linkages of amino acids consisting of the five chemical elements carbon, hydrogen, oxygen, nitrogen and sulfur. The ratio of these elements to each other is very similar for all peptides, regardless of their total mass. This means that, by way of approximation, all peptides can be imagined to be chains of molecules comprised of a hypothetical "average" amino acid, the "averagine" (see Senko, M. W., S. C. Beu and F. W. McLafferty (1995): "Determination of monoisotopic masses and ion populations for large biomolecules from resolved isotopic distributions." Journal of the American Society for Mass Spectrometry 6(4): 229-233). According to this model, this results in an almost linear relationship between the mass m of a peptide and its nominal mass $m_N$, $$m=\lambda_p m_N, \text{ with } \lambda_p=1+4.95\times 10^{-4}.$$

Figure 2:
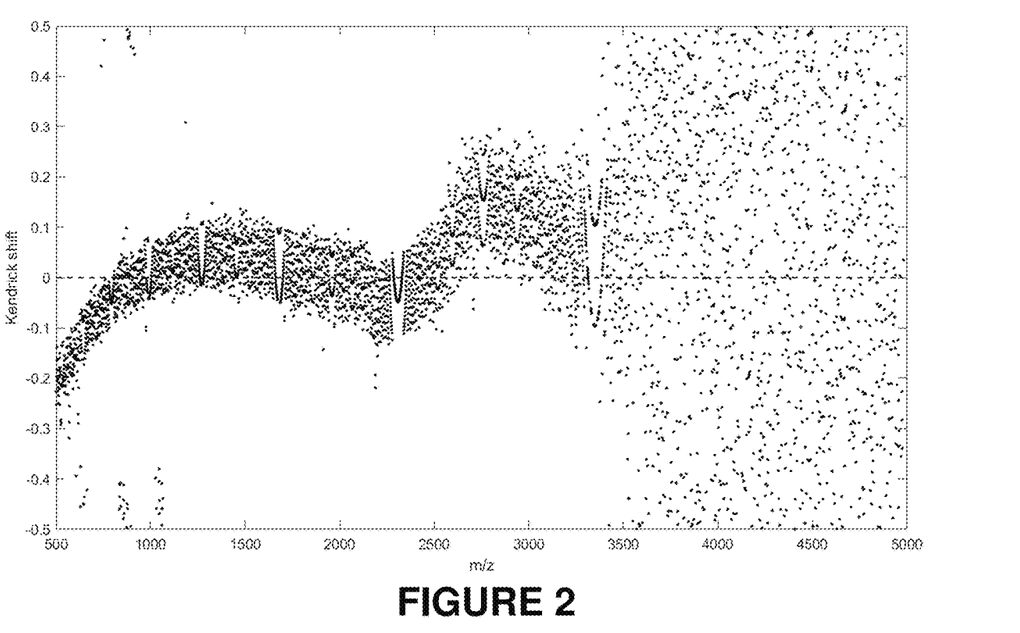
FIG. 2 illustrates a Kendrick diagram of the spectrum from FIG. 1, in which the peptide band is localized around the zero line (similar to WO 2018/072862 A1).
Figure 3:
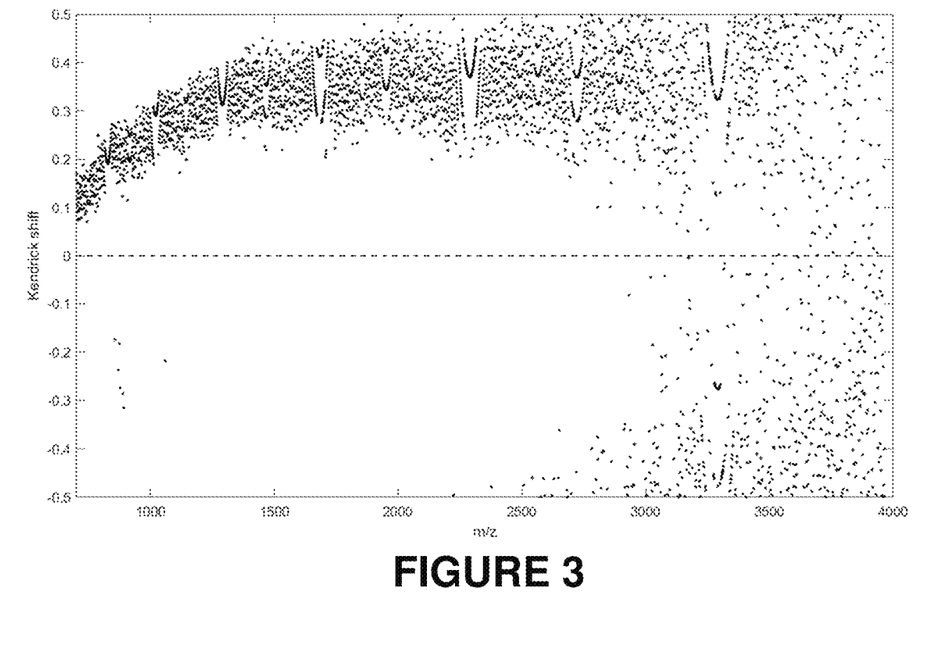
FIG. 3 depicts a Kendrick diagram of a spectrum with a clear mass discrepancy of up to approx. 0.35 daltons (similar to WO 2018/072862 A1).

The large number of different proteins and—given suitable sample preparation, e.g. a digest with an enzyme like trypsin—peptides resulting therefrom in the biological tissue, mean that a typical MALDI spectrum has signal components for peptides in a large mass range. In a Kendrick diagram for the scaling factor $\lambda_p$, the corresponding exact masses appear scattered about the zero line (see FIG. 2). In a real measurement, however, the measurement errors occurring, and thus the accompanying distortion of the mass axis, appear as a vertical shift (see FIG. 3).

Assuming that a measured spectrum is dominated by peptide signals and the mass shift is within ±0.5 dalton, this means that the deviation between the average measured peptide masses in a specific interval of the mass axis and the true peptide masses can be estimated via the first circular moment p of the distribution of the Kendrick shift in this mass interval (see WO 2018/072862 A1). This is mathematically equivalent to calculating a Fourier integral of the spectrum over the interval considered for the frequency $\omega=2\pi/\lambda_p$. The observed mass shift $\Delta$ is approximately given by the complex argument of the moment p by means of $\Delta=\arg(\mu)/2\pi$.

To reduce the relative mass shifts within an ensemble of spectra, the circular moments for each spectrum are determined separately. The average moment over all the spectra serves as a reference; the individual spectra are transformed such that their shifts with respect to the reference value vanish (see WO 2018/072862 A1).

The publication Bajrami B. et al.: Journal of the American Society for Mass Spectrometry, Vol. 20, No. 11, 1 Nov. 2009, pages 2124-2134, discusses effects of chemical modifications of amino acids on the distribution of the peptide mass defects relative to the averagine model.

The publication Melinda L. Toumi et al.: Journal of Proteome Research, Vol. 9, No. 10, 1 Oct. 2010, pages 5492-5495, explains a comparison of the spread of measured averagine peptide mass defects with a theoretical distribution, and derives therefrom an adjusted mass defect filter for the purpose of more precise peptide selection.

The publication Indranil Mitra et al., Anal. Chem., 20 Mar. 2012, 20; 84(6): 3026-3032, provides a more detailed description of the theoretical averagine peptide mass defects as a function of a mass defect filter, and likewise derives an adapted mass defect filter from this for the purpose of more precise peptide selection.

The publication US 2012/0232805 A1 discloses a computerized method and a device for listing one or more amino acid compositions in the field of amino acid analysis.

Having regard to the statements above, there is a need to provide a method with which the mass defects from samples with complex polymer composition can be evaluated. Further objectives to be solved by the invention will be obvious to the specialist skilled in the art in this field when they read the disclosure below.

SUMMARY OF THE INVENTION

The present invention makes use of the fact that the chemical background signal observed in a mass spectrum of biological tissue samples contains components from a plurality of polymer molecules, whose chemical structure has strong regularities. These regularities mean that the masses (mass-to-charge ratios) observed are subject to certain statistical distributions, which are each characteristic of the class of molecule. By analyzing these statistical properties, it is possible to detect and correct any mass shifts which may be present.

The method from WO 2018/072862 A1, mentioned in the introduction, is only suitable for data in which the chemical background signal originates primarily from a single substance class, for example the peptides stated in WO 2018/072862 A1. The extensions described here allow it to also be applied to data which were obtained using other preparation protocols and analytical methods and/or where the background signal has a more complex structure. It is frequently the case, for example, that various classes of molecules can be present together in tissue samples, such as lipids, glycans as well as proteins and peptides in the low to medium mass range.

The essential ideas forming the basis of these extensions are: In addition to proteins and peptides, it is also possible to describe other classes of molecule such as N-glycans and lipids with the aid of relatively simple mass models. The possibly more complex structure of the Kendrick diagram can be taken into account with sufficient precision by using higher circular moments. Relative mass shifts can be estimated by a direct comparison of all the moments considered. A suitably adapted Hough transform can be used to approximately localize linear structures in the circular geometry of the Kendrick diagram. The localization of a complete, connected structure and its assignment to a single class of molecule allow mass errors to be corrected, with simple additional assumptions, even above and beyond ±0.5 dalton.

The invention relates in particular to methods for the evaluation of mass spectrometric measurement data for the analysis of tissue samples, comprising the steps of: (a) providing a tissue sample containing polymers with varying linkages of characteristic molecules, e.g. biopolymers of the type of proteins, peptides, N-glycans and/or lipids, (b) processing the tissue sample in order to prepare at least two types of polymers and molecules derived therefrom and make them accessible for a subsequent mass-spectrometric measurement, (c) acquiring mass spectra from the tissue sample processed, (d) determining the mass shifts of the polymer mass signals shown in the mass spectra, wherein a mass shift represents the deviation of a measured mass signal from the immediately adjacent molecular mass signal to be expected on a mass scale, and the totality of the possible molecular mass signals is calculated by means of a theoretical model of at least one type of polymer, where in order to create a theoretical model of at least one type of polymer, the mass can be assumed to be approximately proportional to the nominal mass, and all natural numbers in a suitably selected range can be taken into consideration as possible nominal masses for this type of polymer, (e) evaluating the mass shifts determined, e.g. comprising (i) calculation of circular moments greater than the first circular moment in order to detect more than one cluster point of Kendrick shifts, and/or (ii) a Hough-type transform for recognizing structures, and (f) assessing a quality of the mass spectra according to the evaluation.

The determination of the mass shifts preferably comprises calculation of the quantity $$\Delta_\lambda(m) = \varphi\left(\frac{m}{\lambda} + \frac{1}{2}\right) - \frac{1}{2}$$

where $\varphi(x)=x-\text{floor}(x)$ (Kendrick shift) for measured mass values m. A scaling factor $\lambda$ is selected such that it corresponds to the average ratio between exact mass and nominal mass of the polymers, for example for N-glycans $\lambda_G=1+3.5\times10^{-4}$ and for proteins/peptides $\lambda_p=1+4.95\times10^{-4}$.

To estimate a Kendrick profile for a mass spectrum: (i) the positions of the local maxima of the mass spectrum can be determined, plotted as a point cloud in the Kendrick diagram, and a distribution function estimated by means of standard methods of density estimation; or (ii) a two-dimensional histogram from the spectral intensities of a mass spectrum in the plane of the Kendrick diagram can be formed, so that the intensities occurring within each histogram tile are summed up and, after normalization in the vertical direction, each column corresponds to a numerical approximation of the Kendrick profile for the relevant mass interval.

The evaluation and assessment of the quality of the mass spectra can consist in determining a deviation between the mass scale used for the acquisition of the mass spectra and a mass scale derived from the mass shifts, in particular such that the evaluation involves: (i) an absolute mass calibration of individual mass spectra by identifying a dominant component and its characteristic for an individual mass spectrum and, from this, determining a correction function for a mass calibration; and/or (ii) a relative correction of the mass scales of an ensemble of mass spectra with respect to each other so that the relative shifts between the mass spectra are minimized.

In various embodiments, the steps to calculate the Kendrick shifts and to calculate circular moments can be combined, and the nth circular moment can be expressed as per the equation $$\mu_{k,n} = \frac{1}{\int_{I_k} \tilde{S}(t)dt} \int_{I_k} \tilde{S}(t)e^{in\omega T}dt, \text{ with } \omega = \frac{2\pi}{\lambda},$$

as a Fourier integral of the continuously interpolated spectrum $\tilde{S}$ over subintervals $I_k$ of the mass scale. Here it is possible to calculate the deviation in the range of the subinterval $I_k$ of the mass scale from at least two circular moments for different n as per the equation $$\Delta_k = \frac{1}{2\pi}\arg\left(\sum_n \mu_{k,n}\bar{\mu}_{k,n}^*\right),$$

where the $\bar{\mu}_{k,n}^*$ designate the complex conjugates of the nth circular moments of a reference Kendrick profile in the subinterval $I_k$. Furthermore, the $\bar{\mu}_{k,n}$ can be reproduced from an ensemble of N spectra $S^j$ (j=1 ... N) and the associated moments $\mu_{k,n}^j$ as per the equation $$\bar{\mu}_{k,n} = \frac{1}{\Sigma_j|\mu_{k,n}^j|^\alpha} \sum_{j=1}^{N} |\mu_{k,n}^j|^\alpha \mu_{k,n}^j,$$

with an exponent $\alpha \in \mathbb{N}_0$, for which it is preferable to choose one of the values 0, 1 or 2.

In various embodiments, the Hough-type transform can be carried out on the mass values $m_i$ determined from an acquired spectrum, to associated Kendrick shifts $\Delta_i$ and appropriately selected density values $p_i$, where the density values $p_i$ can correspond to the spectral intensities of an acquired spectrum, and the $m_i$ to the associated mass values in each case, as per the equation $$H(r, d) = \sum_{i \in L(r,d)} p_i \text{ with}$$

$$L(r, d) = \left\{i : \left|d - \varphi\left(\Delta_i - rm_i + \frac{1}{2}\right) - \frac{1}{2}\right| \leq \frac{\varepsilon}{2}\right\},$$

where r is discretized in a suitably selected range, preferably in the interval $[-10^{-3} \ldots 10^{-3}]$, d is discretized in the interval $[-\frac{1}{2} \ldots \frac{1}{2}]$, and $\varepsilon$ corresponds to the discretization width of d.

In special embodiments, the $m_i$ can correspond to the mass values for local maxima of an acquired spectrum, and the $p_i$ can be chosen to be unity.

The deviation can be determined as per one of the equations (i) $\Delta(m)=\hat{r}m+\hat{d}$ or (ii) $\Delta(m)=\varphi(\hat{r}m+\hat{d}+\frac{1}{2})-\frac{1}{2}$, where $(\hat{r}, \hat{d})$ describes a local maximum of a Hough transform H(r, d), which can correspond to the global maximum of the Hough transform H(r, d).

In various embodiments, the processing of the tissue sample can include the action of agents and/or reagents. Examples of reagents are, in particular, enzymes for a peptide digest such as trypsin, or glycan-cleaving enzymes such as endoglycosidase (e.g. PNGase F). Alternatively, a protein or peptide digest or the cleaving of glycans can be carried out by means of an acidic hydrolysis using acids as reagents. Examples of agents are ambient conditions such as heat or humidity, e.g. while a reactant is acting on the tissue sample. Furthermore, the tissue sample can be subjected to an ultrasonic treatment or several successive cycles of repeated freezing and thawing steps. These treatments facilitate easier access to individual lipid molecules, for example, since they cause the ordered membrane structure in the tissue to be broken up. With MALDI analyses, the choice of matrix substance used and its quantity during sample preparation can also have an effect on the quality and quantity of the classes of biomolecules detected. In various embodiments, the tissue sample can thus comprise treatment with different matrix substances, which can likewise appear themselves as polymerized mass signals in a mass spectrum, in varying quantities.

BRIEF DESCRIPTION OF THE DRAWINGS

The invention can be better understood by referring to the following illustrations. The elements in the illustrations are not necessarily to scale, but are primarily intended to illustrate the principles of the invention (largely schematically). In the illustrations, the same reference characters designate corresponding elements in the different views.

DETAILED DESCRIPTION

While the invention has been described and explained with reference to a number of embodiments, those skilled in the art will recognize that various changes in form and detail can be made hereto without departing from the scope of the technical teaching defined in the enclosed claims.

Figure 4:
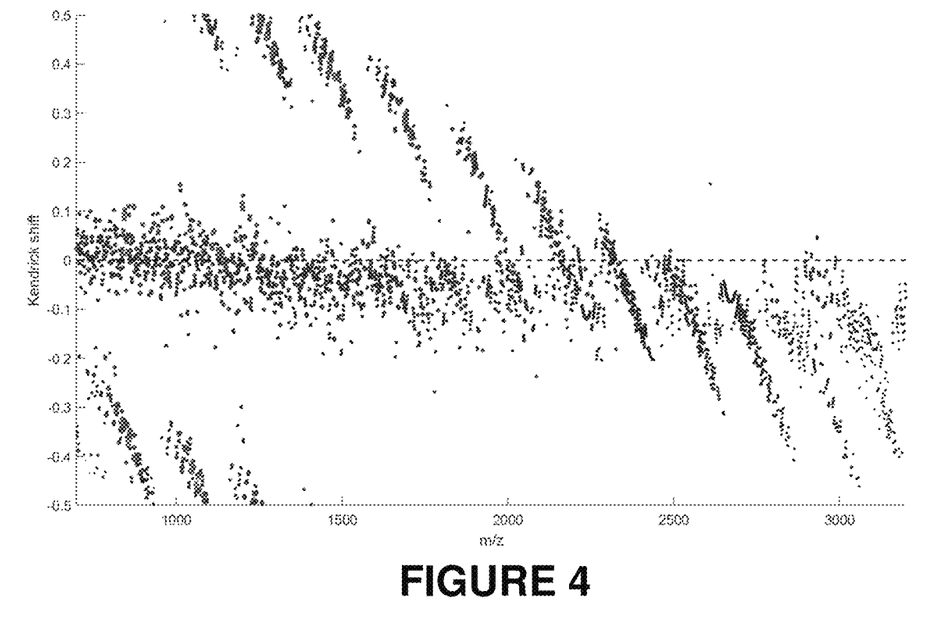
FIG. 4 shows a complex Kendrick diagram of a peptide spectrum with superimposed matrix signal.
Figure 5:
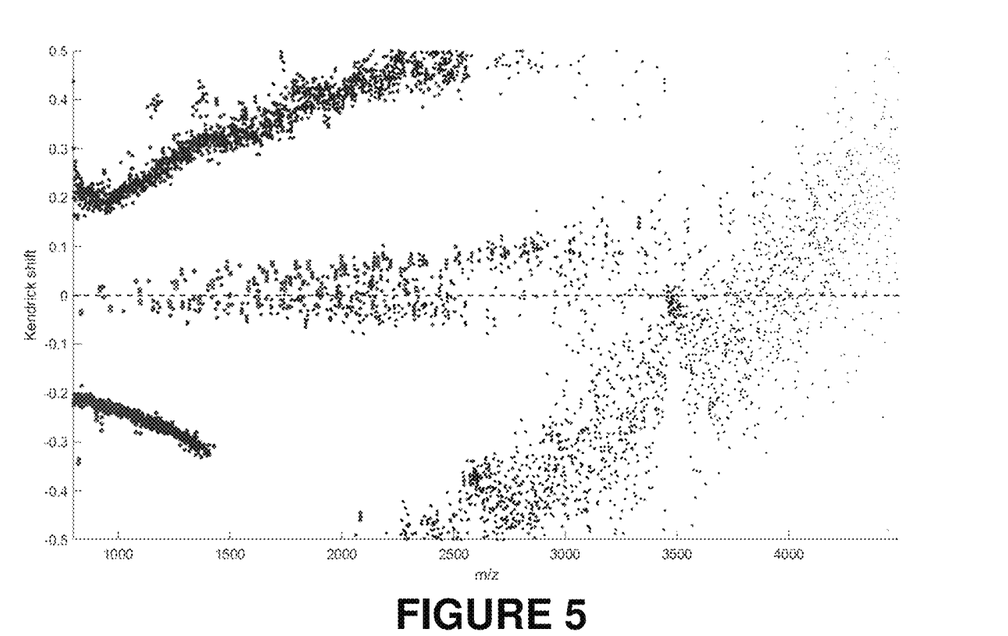
FIG. 5 illustrates a complex Kendrick diagram of an N-glycan spectrum with glycan band (horizontal center), peptide signal (top left and right) and matrix component (bottom left).

The method outlined in the introduction is conditional on there being no significant signal components from other classes of molecules in the spectrum in addition to the class of molecule investigated. When this condition is not fulfilled, further structures appear in the Kendrick diagram in addition to the structure that is actually of relevance, and these may also be superimposed on the former. This situation can even occur with MALDI imaging data obtained from proteins and peptides in the form of MALDI matrix-substance cluster ions (see FIG. 4), but also exists, in particular, with measurements targeted at other classes of molecules (see FIG. 5). In consequence, the first circular moment p known from WO 2018/072862 A1 does not coincide with the cluster point of the Kendrick shifts and thus does not allow a reliable statement to be made about a mass shift which may exist.

An extension of the method is described below which can also be applied when signal components of several classes of molecules superimpose on each other in the spectra. A variety of methods are described which allow both an absolute calibration of individual spectra as well as a relative correction of an ensemble of spectra.

The method is principally suitable for spectral data in which signal components from one or more classes of polymer molecules are present. The term "polymers" is used here for molecules which consist mainly of a combination of several identical or chemically similar groups of atoms. In relation to biopolymers, this includes not only the aforementioned proteins and peptides but particularly glycans, which consist of a tree-like arrangement of monosaccharides (single sugar molecules), or lipids, which contain one or more hydrocarbon chains as key constituents. Matrix substances such as sinapic acid, 2,5-dihydroxybenzoic acid, α-cyanohydroxy cinnamic acid or 2,4,6-trihydroxyacetophenone can also polymerize to clusters and appear in mass spectra as a correspondingly regular background signal.

Hereinafter, particular consideration is given to the class of molecules known as N-glycans, since these are very important for biomedical applications and, at the same time—with suitable sample preparation, e.g. a digest with enzymes such as an endoglycosidase (e.g. peptide n-glycosidase F, PNGaseF)—can be detected with a high signal quality in MALDI imaging data (see Drake, R. R., T. W. Powers, E. E. Jones, E. Bruner, A. S. Mehta and P. M. Angel (2017): "MALDI Mass Spectrometry Imaging of N-Linked Glycans in Cancer Tissues." Advances in Cancer Research 134: 85-116).

The peptide mass model describes the statistical distribution of the exact masses of peptides as a function of their nominal masses. Converting exact masses m to Kendrick mass shifts Δ (relative to a fixed scaling factor λ), one obtains a theoretical, probabilistic model of Kendrick shifts.

This can be described mathematically by a set of probability density functions $P=P(\Delta; m_N)$, which is parameterized by the nominal mass $m_N$. Since the range of values of the Kendrick shift, the interval $[-\frac{1}{2} \ldots +\frac{1}{2}]$, is identified with the circle, these are circular distributions. The probabilistic model P is called the Kendrick profile for the scaling factor $\lambda$.

Figure 6A:
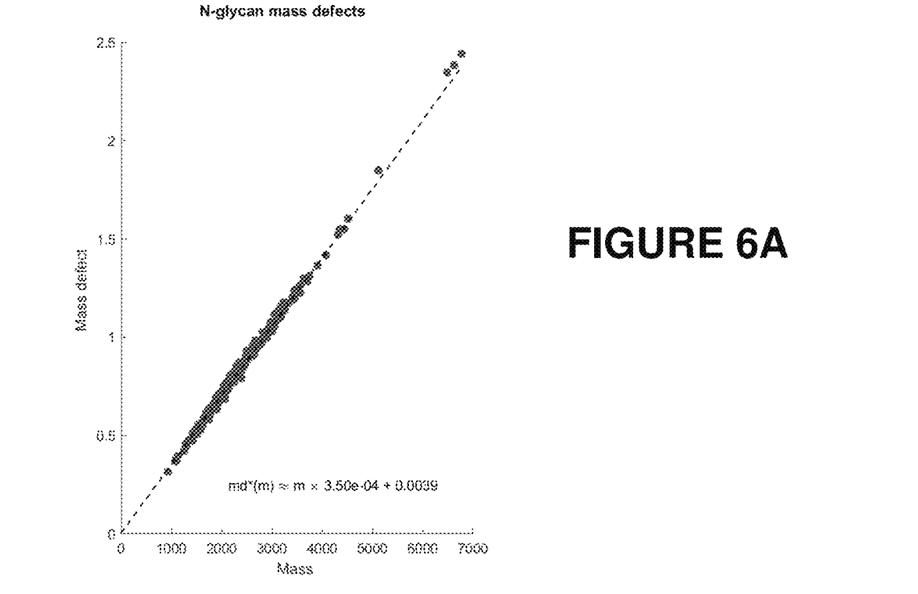
FIG. 6A illustrates the relationship between mass and mass defect for N-glycans.
Figure 6B:
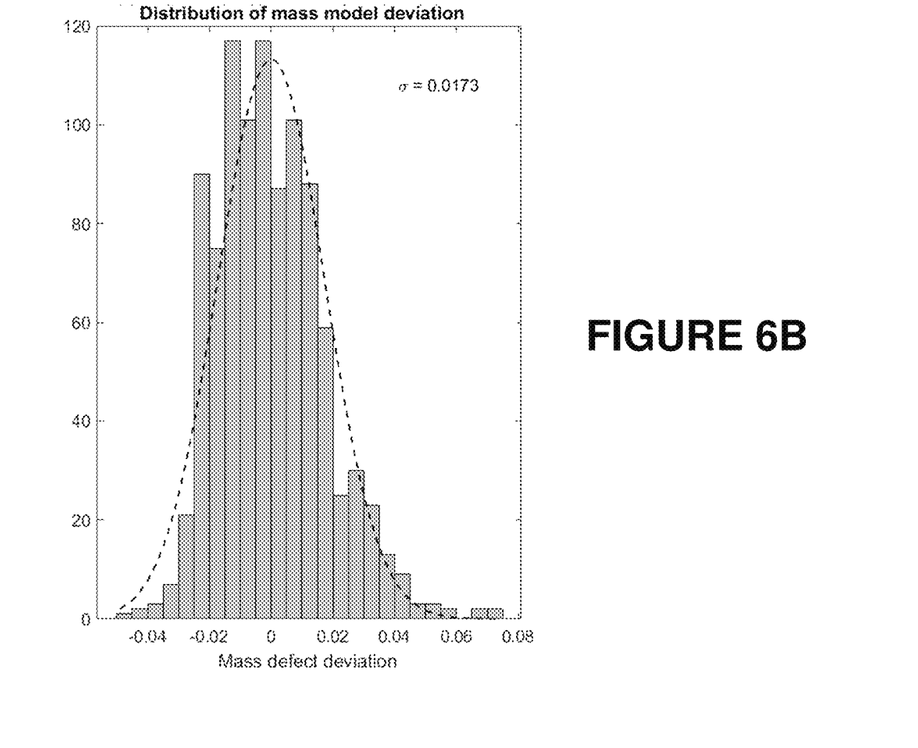
FIG. 6B represents the spread of the mass defects of N-glycans around the expectation value.

When peptides are considered, the theoretical Kendrick profile consists of normal distributions with a mean of zero and a standard deviation which increases with mass (see Wolski, W. E., M. Farrow, A. K. Emde, H. Lehrach, M. Lalowski and K. Reinert (2006): "Analytical model of peptide mass cluster centres with applications." Proteome Sci 4: 18). In general, such a model results when the expected mass defect for a class of molecule is approximately proportional to the nominal mass. This is the case for peptides (see introduction) as well as N-glycans, the associated scaling factor for the latter being $\lambda_G=1+3.5\times10^{-4}$ (see FIG. 6A-B).

For other classes of molecules, the relationship can be more complex, for example a linear dependence with non-zero axis offset. Multi-modal distributions can also appear, with the result that the distribution of the possible mass defects for a given nominal mass has two or more cluster points. More complex relationships can nevertheless also be described by a mathematical model.

The Kendrick profile is an abstract, mathematical model for the relationship between nominal mass and Kendrick shift. A measured spectrum only provides a list of intensities and the corresponding masses, however. Representing a spectrum in a Kendrick diagram allows an initial, visual, qualitative assessment of the said relationship. For a more detailed analysis, the Kendrick profile on which it is based can be estimated from a measured spectrum with the aid of the methods described below. The distortions present in the spectrum (mass shifts, noise) mean that the estimated Kendrick profile will not agree with the theoretical Kendrick profile for the class of molecules considered. The estimated Kendrick profile is therefore called an empirical Kendrick profile hereinafter.

To estimate an empirical Kendrick profile for a spectrum, the positions of the local maxima of the spectrum can be determined, plotted as a point cloud in the Kendrick diagram, and a distribution function estimated using standard methods of density estimation. This is conditional on there being a sufficiently high signal-to-noise ratio in the measured spectrum, which can be the case with average spectra, but is typically not present with individual spectra.

Figure 7:
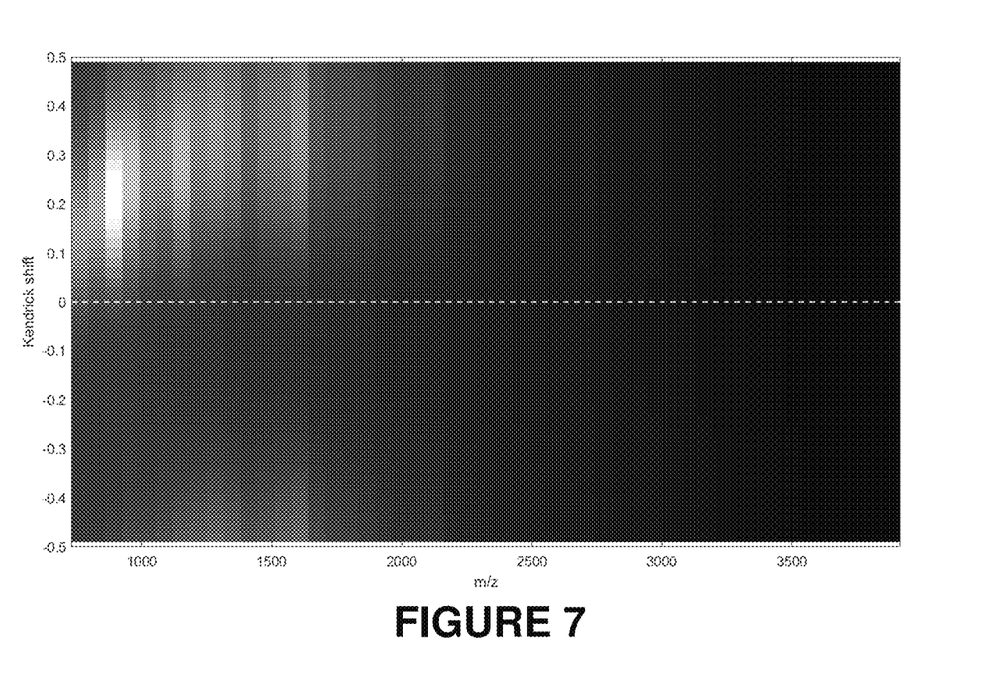
FIG. 7 shows a two-dimensional histogram of a Kendrick profile for the peptide spectrum in FIG. 3.
Figure 8A:
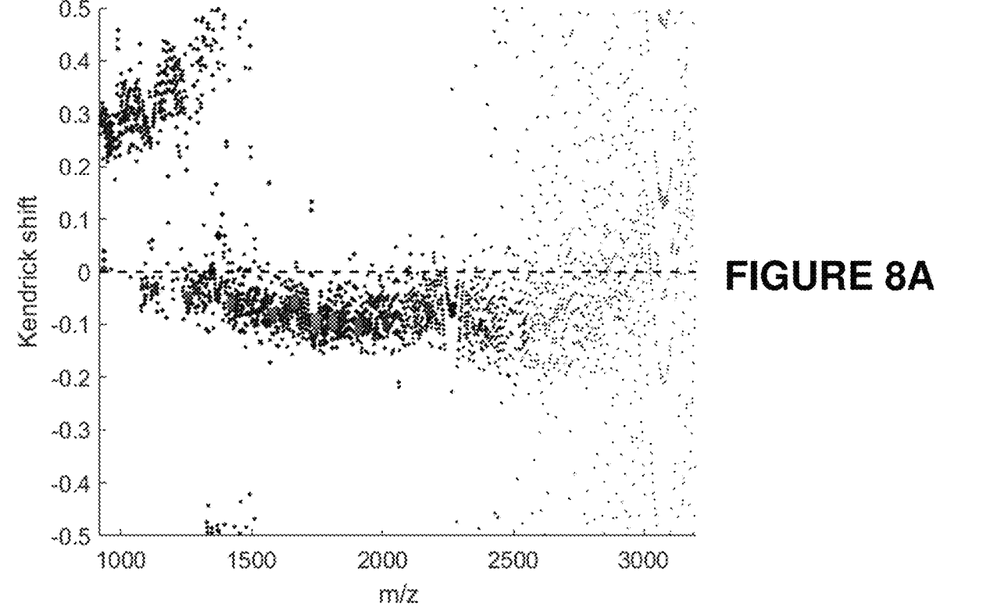
FIG. 8A illustrates a point cloud representation of a Kendrick profile for glycan spectra with a moderate mass shift.
Figure 8B:
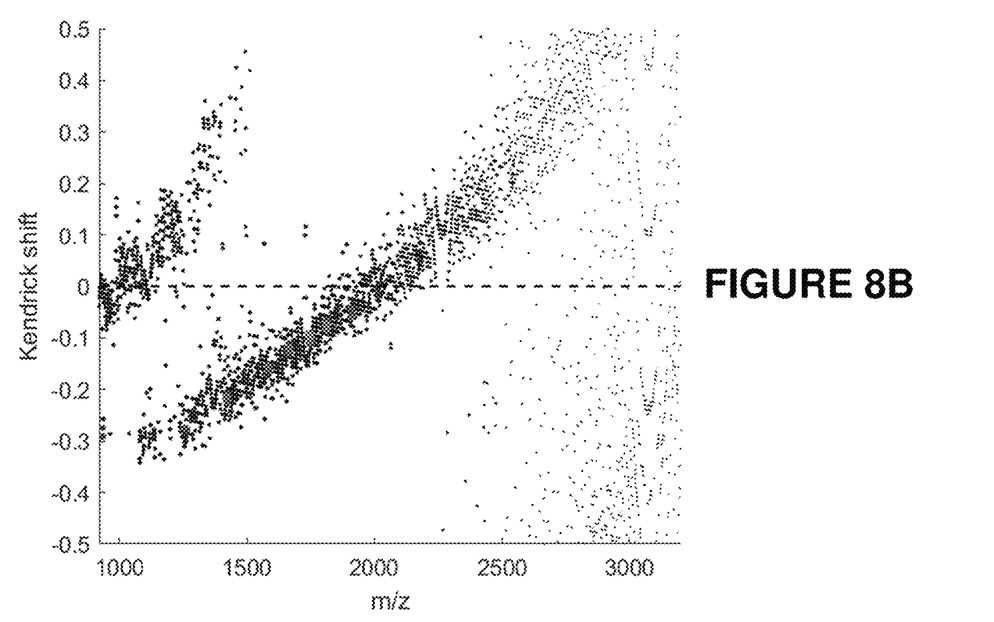
FIG. 8B illustrates a point cloud representation of a Kendrick profile for glycan spectra with a strong mass shift.

Alternatively, a two-dimensional histogram can be formed in the plane of the Kendrick diagram from the spectral intensities of a spectrum so that the intensities occurring within each histogram tile are summed (see FIG. 7). After normalization in the vertical direction, each column corresponds to a numerical approximation of the Kendrick profile for the corresponding mass interval. This approach can also be used with noisier spectra and is therefore preferred.

The information contained in a Kendrick profile can be used in two ways: On the one hand, for an ensemble of measured spectra, corrections for each individual spectrum can be determined by comparing the associated profiles so that the relative shifts between the spectra are minimized. On the other hand, the dominant component and its characteristic can be determined for an individual spectrum and used in turn to determine a correction function for a mass calibration. Both of these methods are illustrated below.

With unimodal, symmetric distributions, the first circular moment can be used to determine the position of the cluster point of the distribution. This is not possible with asymmetric or multimodal distributions. It is, however, possible to determine the relative shift by comparing two moments for two different Kendrick profiles at the same mass position. But this method becomes numerically unstable and loses accuracy if the respective moments are close to zero in absolute terms, which is often the case with multimodal distributions.

To overcome this, not only the first circular moment is considered, but further, higher moments, too, and the relative shift between two profiles is determined via a weighted averaging. The mass axis is divided up into subintervals $I_k$ and a spectrum S is considered, which is interpolated by a continuous function $\tilde{S}(m)$. The nth circular moment for the Kendrick profile in the interval $I_k$ is calculated with $$\mu_{k,n} = \frac{1}{\int_{I_k} \tilde{S}(t)dt} \int_{I_k} \tilde{S}(t)e^{in\omega t}dt, \text{ with } \omega = \frac{2\pi}{\lambda}.$$

For an ensemble of N spectra $S^j$ (j=1 ... N) with a common mass axis, the corresponding moments $\mu_{k,n}^j$ are calculated in this way, as are the average moments $$\bar{\mu}_{k,n} = \frac{1}{\Sigma_j |\mu_{k,n}^j|^\alpha} \sum_{j=1}^{N} |\mu_{k,n}^j|^\alpha \mu_{k,n}^j,$$

which describe the reference profile. The exponent $\alpha \in \mathbb{N}_0$ describes the extent to which the absolute values of the individual moments enter into the weighting, typical values are $\alpha \in \{0, 1, 2\}$.

For the jth spectrum, the relative mass shift in the subinterval $I_k$ is now calculated with respect to the reference profile with $$\Delta_k^j = \frac{1}{2\pi} \arg\left(\sum_n \mu_{k,n}^j \bar{\mu}_{k,n}^*\right),$$

where z* is called the complex conjugate of an arbitrary complex number z (here μ).

The individual shifts $\Delta_k^j$ are assigned to the midpoints of the subintervals $I_k$ and interpolated over the whole mass axis (typically by means of linear interpolation). A shift vector is thus obtained for the transform of the mass axis of the jth spectrum.

For a more accurate normalization, or a correction, of absolute mass shifts, it is helpful to identify the distribution component associated with a given class of molecule in a Kendrick profile. In many cases, these are approximately linear structures which can be found with the aid of the Hough transform known from image processing, see U.S. Pat. No. 3,069,654. Known uses of Hough-type transforms in the field of mass spectrometry are confined to those which locate morphologies or textures in two-dimensional mass spectrometric images; see for example the publication US 2017/0221687 A1. Since the topology of the Kendrick profile corresponds to that of a cylinder because of the identicalness of the upper and lower edge, an appropriately adapted transform is used hereinafter.

The conventional Hough transform operates on images which are defined in a plane, two-dimensional space. The Hough transform H for such an image represents a depiction which indicates, for every point in a likewise two-dimensional parameter space, the intensity with which the straight line parameterized by the respective point can be found in the original image. Variants of the Hough transform are known for other parametrizable geometric figures, such as circles or ellipses.

In the case considered, the empirical Kendrick profile, which is defined not in a two-dimensional space, but in a cylindrical space, replaces the original image. The linear objects sought in this space are parametrized by a gradient r and an offset d, and are described by equations of the type $\Delta(m)=\varphi(rm+d+\frac{1}{2})-\frac{1}{2}$. The cylindrical Hough transform for locating linear structures in a Kendrick profile is now defined as follows.

Let an empirical Kendrick profile as described above be represented by a 2D histogram. For the ith histogram tile, $m_i$ and $\Delta_i$ are the interpolation points on the mass axis or Kendrick shift axis respectively, and $p_i$ the corresponding density value of the Kendrick profile. The cylindrical Hough transform H is then given by $$H(r, d) = \sum_{i \in L(r,d)} p_i \text{ with}$$

$$L(r, d) = \left\{ i : \left| d - \varphi\left(\Delta_i - rm_i + \frac{1}{2}\right) - \frac{1}{2} \right| \leq \frac{\varepsilon}{2} \right\},$$

Here the gradient r describes the deviation from the scaling factor $\lambda$, and d the constant offset of the mass shift in the range $[-\frac{1}{2} \ldots +\frac{1}{2}]$. Appropriate discretizations are chosen for both quantities; $\varepsilon$ corresponds to the discretization width for d.

If the Kendrick profile is described by means of a point cloud, i.e. as a sequence of Kendrick shifts $\Delta_i$ and corresponding masses $m_i$, the cylindrical Hough transform is calculated in the same way by assuming that the $p_i$ are unity.

Figure 9A:
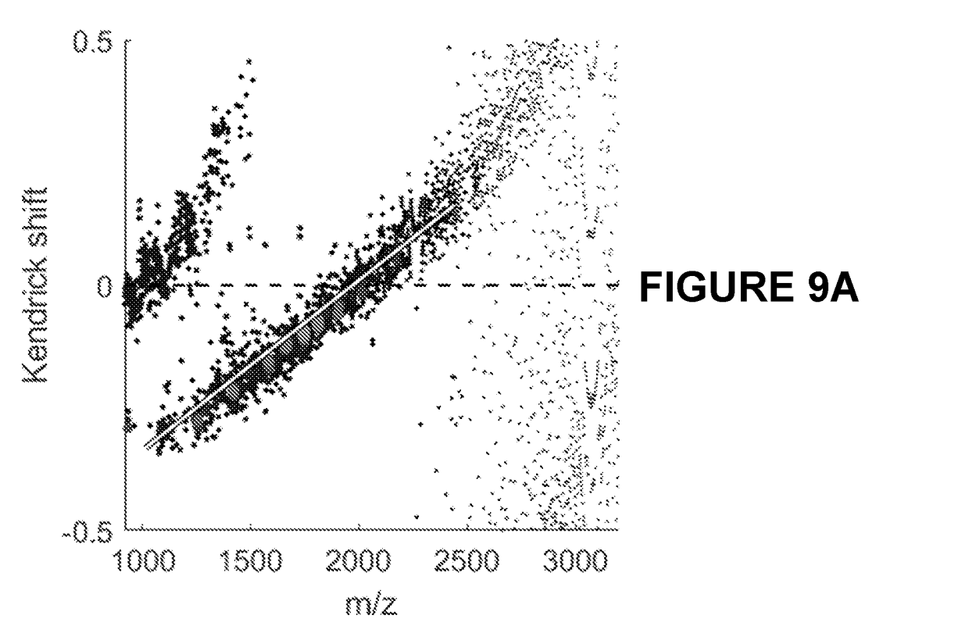
FIG. 9A illustrates the Kendrick profile from FIG. 8B, including highlighting of a dominant structure (solid double line).
Figure 9B:
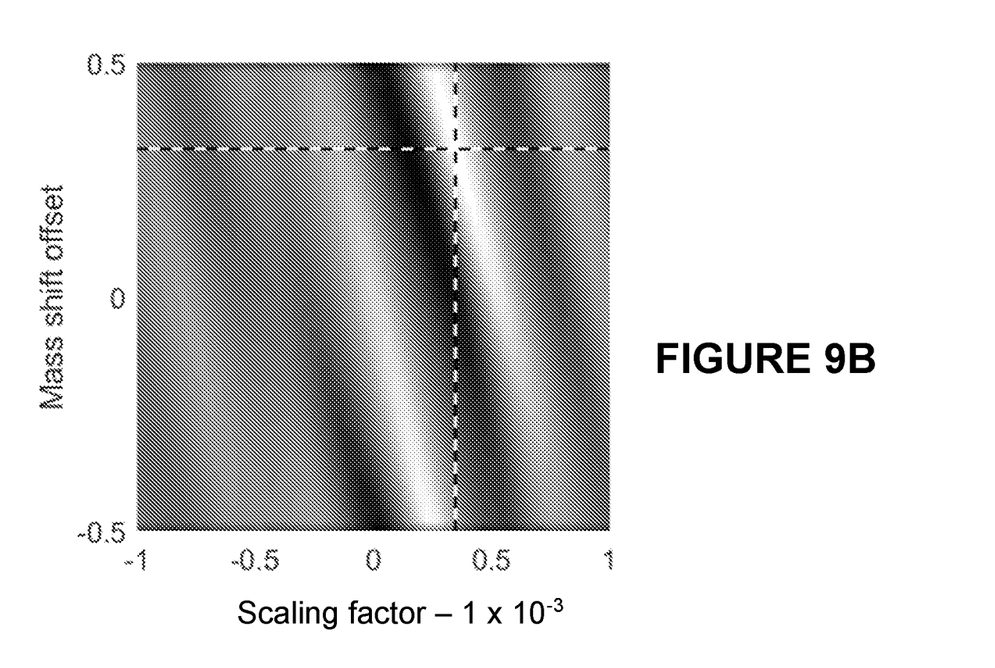
FIG. 9B shows a cylindrical Hough transform for the Kendrick profile from FIGS. 8B and 9A. The cross-hair marks the absolute maximum of the Hough transform and provides the position of the dominant structure in the Kendrick profile.
Figure 9C:
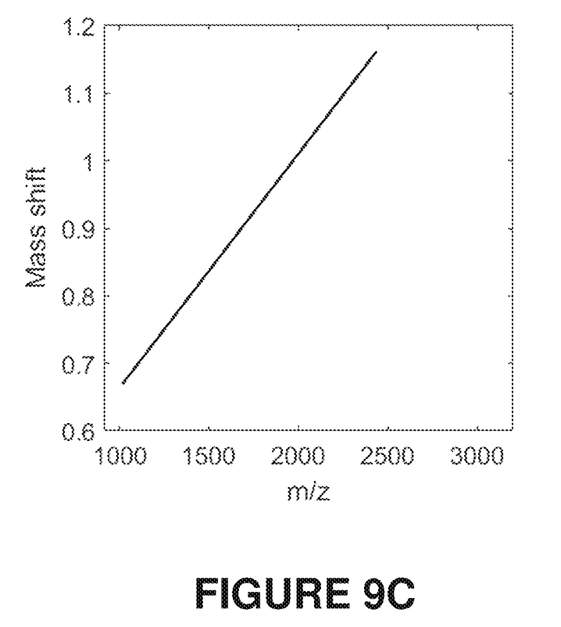
FIG. 9C depicts a correction function for the mass axis obtained from the Hough transform in FIG. 9B, which exceeds 0.5 dalton.

Linear structures in the Kendrick profile can now be localized via local maxima in the Hough transform (see FIG. 9A-C). If $(\hat{r}, \hat{d})$ is the position of such a local maximum, this corresponds to a linear structure in the Kendrick profile, whose characteristic is described by $$\Delta(m)=\varphi(\hat{r}m+\hat{d}+\frac{1}{2})-\frac{1}{2}.$$

The absolute maximum of the Hough transform can thus be assigned to the dominant class of molecules (see FIG. 9A-C). Assuming that this is the class of molecules considered for the particular investigation (e.g. N-glycans), for which the Kendrick profile was calculated, a shift vector for the correction of the mass axis of the spectrum considered results in turn from the characteristic $\Delta(m)$. Assuming, in addition, that the absolute mass error is within ±0.5 dalton for small masses, and that it increases rather than decreases for larger masses, the mass error of a measured spectrum can thus be determined over the whole mass axis, even beyond ±0.5 dalton. To this end, the "developed" shift $\tilde{\Delta}(m)=\hat{r}m+\hat{d}$ is used instead of the Kendrick shift $\Delta(m)$.

Figure 10:
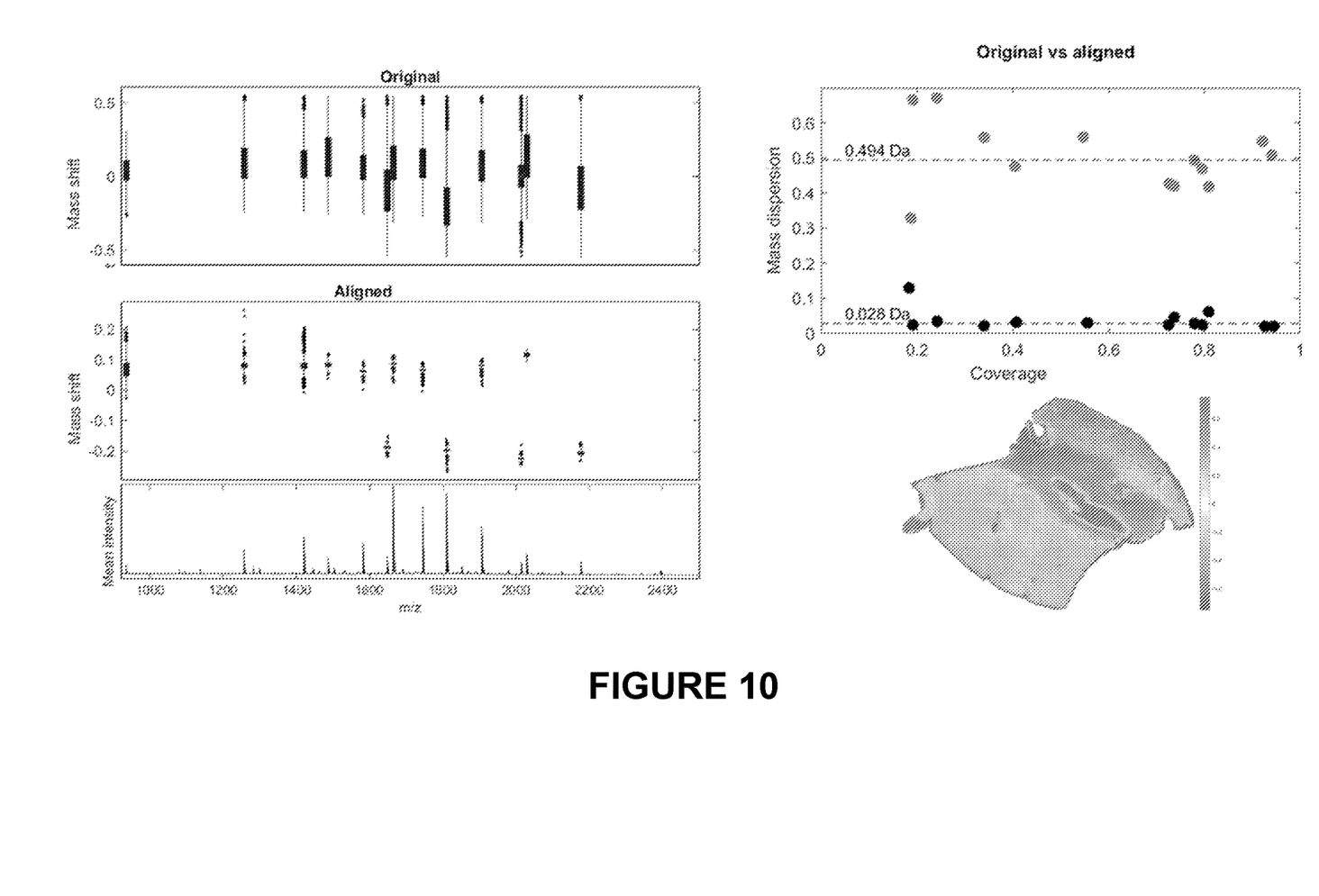
FIG. 10 illustrates an example of a successful mass axis correction, whose function was obtained from MALDI-TOF imaging data on the basis of the glycan signals contained therein.

FIG. 10 shows an example of measurement data of a tissue section cut from FFPE samples (FFPE=formalin-fixed paraffin-embedded) of human tissue of the hepatocellular carcinoma (HCC) with a thickness of five micrometers (Hoshida et. al., Cancer Res. 15 Sep. 2009; 69(18): 7385-7392), prepared according to a standard N-glycan imaging protocol (Powers et. al., Anal. Chem., 15 Oct. 2013; 85(20): 9799-9806) and analyzed with a reflector-mode MALDI-TOF mass spectrometer at m/z 900-3200 and with a 50-micrometer spatial resolution. The mass shift determined with the methods described here was between 266 mDa and 496 mDa over several tissue sections, and using the correction of the mass axis proposed here in this disclosure it was possible to reduce it to values between 18 mDa and 28 mDa, which means that the mass accuracy was significantly improved.

FIG. 10 depicts the data and correction for the tissue section with the largest mass deviation. Comparative measurements with an ultra-high resolution Fourier transform ion cyclotron resonance mass spectrometer (FT-ICR) with a spatial resolution of 200 micrometers, which were obtained from adjacent tissue sections of the above-mentioned HCC samples, showed a maximum mass deviation of 25 ppm between corrected MALDI-TOF and MALDI FT-ICR data, and thus confirmed a high absolute mass accuracy of the mass scales.

The invention has been described above with reference to different, specific example embodiments. It is to be understood, however, that various aspects or details of the embodiments described can be modified without deviating from the scope of the invention. In particular, features and measures disclosed in connection with different embodiments can be combined as desired if this appears feasible to a person skilled in the art. Moreover, the above description serves only as an illustration of the invention and not as a limitation of the scope of protection, which is exclusively defined by the appended claims, taking into account any equivalents which may possibly exist.

The invention claimed is:

1. A method for the evaluation of mass spectrometric measurement data for the analysis of tissue samples, comprising the steps of:
    (a) providing a tissue sample which contains polymers having varying linkages of characteristic molecules;
    (b) processing the tissue sample in order to prepare at least two types of polymers and molecules derived therefrom and render them accessible for a subsequent mass-spectrometric measurement;
    (c) acquiring mass spectra of the processed tissue sample;
    (d) determining the mass shift of the polymer mass signals imaged in the mass spectra, where a mass shift represents the deviation of a measured mass signal from the adjacent molecular mass signal to be expected on a mass scale, and the totality of the molecular mass signals to be expected is calculated using a theoretical model of at least one type of polymer;
    (e) evaluating the mass shifts determined; and
    (f) assessing a quality of the mass spectra according to the evaluation.

2. The method according to claim 1, wherein, in order to create a theoretical model of at least one type of polymer, the mass is assumed to be approximately proportional to the nominal mass, and all natural numbers in a suitably selected range are taken into consideration as possible nominal masses for this type of polymer.

3. The method according to claim 1, wherein the polymers comprise biopolymers of the type of proteins, peptides, N-glycans and/or lipids.

4. The method according to claim 1, wherein the determination of the mass shifts comprises the calculation of the quantity $$\Delta_\lambda(m) = \varphi\left(\frac{m}{\lambda} + \frac{1}{2}\right) - \frac{1}{2},$$

where $\varphi(x)=x-\text{floor}(x)$ (Kendrick shift) for measured mass values m, and a scaling factor $\lambda$ is selected such that it corresponds to the average ratio between exact mass and nominal mass of the polymers.

5. The method according to claim 4, wherein the scaling factor for N-glycans is $\lambda_G=1+3.5\times10^{-4}$, and for proteins and peptides $\lambda_P=1+4.95\times10^{-4}$.

6. The method according to claim 4, wherein the Kendrick profile for a mass spectrum is estimated by: (i) determining the positions of the local maxima of the mass spectrum, plotting them as a point cloud in the Kendrick diagram, and estimating a distribution function by means of standard methods of density estimation; or (ii) forming a two-dimensional histogram from the spectral intensities of a mass spectrum in the plane of the Kendrick diagram so that the intensities occurring in each histogram tile are summed up and, after normalization in the vertical direction, each column corresponds to a numerical approximation of the Kendrick profile for the relevant mass interval.

7. The method according to claim 4, wherein the evaluation comprises: (i) the calculation of circular moments greater than the first circular moment in order to detect more than one cluster point of Kendrick shifts; and/or (ii) a Hough-type transform for recognizing the structure.

8. The method according to claim 7, wherein the steps to calculate the Kendrick shifts and to calculate circular moments are combined and the nth circular moment is expressed as per the equation $$\mu_{k,n} = \frac{1}{\int_{I_k} \tilde{S}(t)dt} \int_{I_k} \tilde{S}(t)e^{in\omega t}dt, \text{ with } \omega = \frac{2\pi}{\lambda},$$

as a Fourier integral of the continuously interpolated spectrum $\tilde{S}$ over subintervals $I_k$ of the mass scale.

9. The method according to claim 8, wherein the deviation in the range of the subinterval $I_k$ of the mass scale is calculated from at least two circular moments for different n as per the equation $$\Delta_k = \frac{1}{2\pi}\arg\left(\sum_n \mu_{k,n}\bar{\mu}_{k,n}^*\right),$$

where the $\bar{\mu}_{k,n}^*$ designate the complex conjugates of the nth circular moments of a reference Kendrick profile in the subinterval $I_k$.

10. The method according to claim 9, wherein the $\bar{\mu}_{k,n}$ are formed from an ensemble of N spectra $S^j$ (j=1 ... N) and the associated moments $\mu_{k,n}^j$ as per the equation $$\bar{\mu}_{k,n} = \frac{1}{\Sigma_j|\mu_{k,n}^j|^\alpha}\sum_{j=1}^{N}|\mu_{k,n}^j|^\alpha \mu_{k,n}^j,$$

with an exponent $\alpha\epsilon\mathbb{N}_0$.

11. The method according to claim 10, wherein one of the values 0, 1 or 2 is chosen for the exponent $\alpha$.

12. The method according to claim 7, wherein the Hough-type transform is carried out on the mass values $m_i$ determined from an acquired spectrum, associated Kendrick shifts $\Delta_i$ and appropriately selected density values $p_i$ as per the equation $$H(r, d) = \sum_{i \in L(r,d)} p_i \text{ with}$$

$$L(r, d) = \left\{i : \left|d - \varphi\left(\Delta_i - rm_i + \frac{1}{2}\right) - \frac{1}{2}\right| \leq \frac{\varepsilon}{2}\right\},$$

where r is discretized in a suitably selected range, d is discretized in the interval $[-\frac{1}{2} \ldots \frac{1}{2}]$, and $\varepsilon$ corresponds to the discretization of d.

13. The method according to claim 12, wherein r is discretized in the interval $[-10^{-3} \ldots 10^{-3}]$.

14. The method according to claim 12, wherein the density values $p_i$ correspond to the spectral intensities of an acquired spectrum, and the $m_i$ to the respectively associated mass values.

15. The method according to claim 12, wherein the $m_i$ correspond to the mass values for local maxima of an acquired spectrum and the $p_i$ are chosen to be unity.

16. The method according to claim 1, wherein the evaluation and the assessment of the quality of the mass spectra encompasses determining a deviation between the mass scale used for the acquisition of the mass spectra and a mass scale derived from the mass shifts.

17. The method according to claim 16, wherein the evaluation comprises: (i) an absolute mass calibration of individual mass spectra by identifying a dominant component and its characteristic for an individual mass spectrum and, from this, determining a correction function for a mass calibration; and/or (ii) a relative correction of the mass scales of an ensemble of mass spectra with respect to each other so that the relative shifts between the mass spectra are minimized.

18. The method according to claim 16, wherein the deviation is determined as per one of the equations: (i) $\Delta(m)=\hat{r}m+\hat{d}$; or (ii) $\Delta(m)=\varphi(\hat{r}m+\hat{d}+\frac{1}{2})-\frac{1}{2}$, where $(\hat{r}, \hat{d})$ describes a local maximum of a Hough transform H(r, d).

19. The method according to claim 18, wherein the local maximum $(\hat{r}, \hat{d})$ corresponds to the global maximum of the Hough transform H(r, d).

20. The method according to claim 1, wherein the processing of the tissue sample includes the action of agents and/or reagents.

* * * * *